United States Patent [19]

Prockop et al.

[11] Patent Number: 5,405,757
[45] Date of Patent: Apr. 11, 1995

[54] SYNTHESIS OF HUMAN PROCOLLAGENS AND COLLAGENS IN RECOMBINANT DNA SYSTEMS

[75] Inventors: Darwin J. Prockop, Philadelphia, Pa.; Leena Ala-Kokko, Toivontie, Finland; Andrzej Fertala; Aleksander Sieron, both of Philadelphia, Pa.; Kari I. Kivirikko, Laamsantie, Finland; Amy Geddis, Philadelphia, Pa.

[73] Assignee: Thomas Jefferson University, Philadelphia, Pa.

[21] Appl. No.: 37,728

[22] Filed: Mar. 24, 1993

Related U.S. Application Data

[63] Continuation of Ser. No. 780,899, Oct. 23, 1991, abandoned.

[51] Int. Cl.$^6$ .......................... C07K 13/00; C12N 5/22; C12N 15/12; C12N 15/85
[52] U.S. Cl. ................................ 435/69.1; 435/240.2; 435/172.3; 435/70.3; 530/356
[58] Field of Search ................ 435/69.1, 69.8, 172.3, 435/320.1, 240.1, 240.2; 530/356; 536/23.5, 24.1; 935/32, 34, 49, 51

[56] References Cited

PUBLICATIONS

Prockop, D. J. et al. "Expression of Type I Procollagen Genes," in *Cell & Molecular Biology of Vertebrate Hard Tissues*, pp. 141–160 (1988).
Fertala, A. et al. *Biochem. J.* 2981 31–37 (1994).
Dickson, L. A. et al. *PNAS* 81:4524–4528 (1994).
Peltonen, L. et al. *PNAS* 77:162–166 (1980).
Ahmad et al., "A stop codon in the gene for type II procollagen (COL2A1) causes one variant of arthro-ophthalmapathy (the Stickler syndrome)" *Am. J. Hum. Genet.*, 47:A206, 1990.
Ala-Kokko et al., "Single base mutation in the type II procollagen (COL2A1) as a cause of primary osteoarthritis associated with a mold chondrodysplasia" *Proc. Natl. Acad. Sci. U.S.A.*, 87:6565–6568, 1990.
Anderson et al., "Spondyloepiphyseal Dysplasia Congenita: Genetic Linkage to Type II Collagen (COL-2A1)" *Am. J. Hum. Genet.*, 46:896–901, 1990).
Aulthouse et al., "Expression of the Human Chondrocyte Phenotype In Vitro," *In Vitro Dev. Biol.*, 25:659–668. 1989.
Bruckner and Prockop, "Proteolytic Enzymes as Probes for the Triple-Helical Conformation of Procollagen, " *Anal. Biochemistry* 110:360, 1981.
Elima and Vuorio, "Expression of mRNAs for collagens and other matrix components in dedifferentiating and redifferentiating human chondrocytes in culture," *FEBS Lett.*, 258:195–198, 1989.
Cheah et al., "Identification and characterization of the human type II collagen gene (COL2A1)" *Proc. Natl. Acad. Sci. USA*, 82:2555–2559, 1985.
Francomano et al., "The Stickler Syndrome: Evidence for Close Linkage to the Structural Gene for Type II Collagen," *Genomics*, 1:293–296, 1987.
Prockop and Kivirikko, "Heritable Diseases of Collagen," *N. Engl. J. Med.*, 311:376–386, 1984.
Knowlton et al., "Genetic Linkage Analysis of Hereditary Arthro–Ophthalmopathy (Stickler Syndrome) and the Type II Procollagen Gene," *Am. J. Hum. Genet.*, 45:681–688, 1989.

(List continued on next page.)

Primary Examiner—Robert A. Wax
Assistant Examiner—Dian C. Jacobson
Attorney, Agent, or Firm—Woodcock Washburn Kurtz Mackiewicz & Norris

[57] ABSTRACT

The invention is stably transfected cells, substantially all of which contain at least one human collagen gene and express fibrillar collagen molecules derived using methods for synthesizing collagen and collagen fibrils in said cell lines, and methods for treatment of disorders in humans using said collagen derived from said stable cell lines.

25 Claims, 3 Drawing Sheets

OTHER PUBLICATIONS

Knowlton et al., "Genetic Linkage of a Polymorphism in the Type II Procollagen Gene (COL2A1) to Primary Osteoarthritis Associated with Mild Chondrodysplasia," *N. Engl. J. Med.*, 322:526–530, 1990.

Law et al., "A Stable Bovine Papillomavirus Hybrid Plasmid That Expresses a Dominant Selective Trait," *Molec. Cell Biol.*, 3:2110–2115, 1983.

Lee et al., "Identification of the Molecular Defect in a Family with Spondyloepiphyseal Dysplasia," *Science*, 244:978–980, 1989.

Lee et al., *J. Biol. Chem.*, 264:20683–20687 (1989).

Palotie et al., "Predisposition to Familial Osteoarthriosis Linked to Type II Collagen Gene," *The Lancet*, I:924–927, 1989.

Tiller et al., "Tandem duplication within a type II collagen gene (COL2A1) exon in an individual with as spondyloepiphyseal dysplasia," *Proc. Natl. Acad. Sci. U.S.A.*, 87:3889–3893, 1990.

Vissing et al., "Glycine to Serine Substitution in the Triple Helical Domain of Pro-$\alpha$1 (II) Collagen Results in a Lethal perinatal Form of Short–limbed Dwarfism," *J. Biol. Chem.*, 264:18265–18267, 1990.

Bornstein et al., "Regulatory elements in the first intron contribute to transcriptional control of the human $\alpha$a (I) collagen gene," *Proc. Natl. Acad. Sci. U.S.A.*, 84:8869–8873, 1987.

Ala–Kokko et al., Matrix, 10(4):234, Jun. 13–16, 1990.

Olsen et al., "High Levels of Expression of a Minigene Version of the Human Pro$\alpha$a(I) Collagen Gene in Stably Transfected Mouse Fibroblasts," *J. Biol. Chem.*, 266:1117–1121, 1991.

de Wet et al., "Synthesis of a Shortened Pro–$\alpha$2(I) Chain and Decreased Synthesis of Pro–$\alpha$2(I) Chains in a Proband with Osteogenesis Imperfecta," *Journal of Biological Chemistry*, 258:7721–7728, 1983.

Laemmli, U.K., "Cleavage of Structural Proteins during the Assembly of the Head of Bacteriophage T4," *Nature*, 227:680–685, 1970.

Ala–Kokko et al., "Expression of a Human Cartilage Procollagen Gene (CL2A1) in Mouse 3T3 Cells," *J. of Biol. Chem.*, 266:14175–14178, 1991.

Proα1(I) →   — ←Proα1(I)
              ←pCα1(I)

SYNTHESIS OF HUMAN PROCOLLAGENS AND COLLAGENS IN RECOMBINANT DNA SYSTEMS

INTRODUCTION

This invention was made in the course of research supported in part by NIH grants AR38188 and AR39740. The Government has certain rights in this invention.

This is a continuation of application Ser. No. 780,899, filed Oct. 23, 1991, now abandoned.

BACKGROUND OF THE INVENTION

Expression of many exogenous genes is readily obtained in a variety of recombinant host-vector systems, but becomes difficult to obtain if the protein normally requires extensive post-translational processing. This is the likely reason that expression in a fully recombinant system has not been reported for any of the major fibrillar collagens that require processing by eight or more post-translational enzymes. See Prockop and Kivirikko, N. Engl. J. Med., 311:376–386 (1984).

Schnieke et al., Proc. Natl. Acad Sci. U.S.A., 84:8869–8873 (1987) and Lee et al., J. Biol. Chem., 264:20683–20687 (1989), disclose rescue experiments in two different systems that synthesized only one of the two chains for type I procollagen. Schnieke et al. reported that a gene for the human fibrillar collagen proα1(I) chain, the COL1A1 gene, can be expressed in mouse fibroblasts and the chains are used to assemble molecules of type I procollagen, the precursor of type I collagen. However, in this system the proα2(I) chains found in the same molecule are of mouse origin. In the system of Lee et al. the proα1(I) chains are of rat origin. Thus, synthesis of a procollagen molecule in which all three chains are derived from an exogenous gene was not obtained by either Schnieke et al. or Lee et al.

Failure to obtain expression of genes for fibrillar collagens in a fully recombinant system has hampered attempts to study the normal structure-function relationships of the proteins and to study the effects of mutations. In particular, mutations in the gene for type II procollagen have recently been implicated as the cause of several human diseases, Anderson et al., Am. J. Hum. Genet., 46:896–901 (1990); Tiller et al., Proc. Natl. Acad. Sci. U.S.A., 87:3889–3893, 1990; Vissing et al., J. Biol. Chem., 264:18265–18267 (1990); Lee et al., Science, 244:978–980 (1989); Francomano et al., Genomics, 1:293–296 (1987); Knowlton et al., Am. J. Hum. Genet., 45:681–688 (1989); Ahmad et al., Am. J. Hum. Genet., 47:A206 (1990); Palotie et al., The Lancet, I:9-24–927 (1989); Knowlton et al., N. Engl. J. Med., 322:526–530 (1990); Ala-Kokko, L., Baldwin et al., Proc. Natl. Acad. Sci. U.S.A., 87:6565–6568 (1990), but because adequate numbers of human cartilage cells are difficult to obtain and because human chondrocytes readily lose their phenotype in culture, Elima and Vuorio, FEBS Lett., 258:195–198 (1989); Aulthouse et al., In Vitro Dev. Biol., 25:659–668 (1989), the causal relationship between a mutation in the gene and the biological function of the protein has proven elusive.

Also, failure to obtain expression of genes for human fibrillar collagens has made it impossible to prepare human fibrillar procollagens and collagens that have a number of therapeutic uses in man and that will not produce the undesirable immune responses that have been encountered with use of collagen from animal sources.

SUMMARY OF THE INVENTION

The present invention involves the preparation of gene constructs that contain collagen genes of human and other origins. One of the gene constructs is hybrid of a human gene for type I procollagen (COL1A1) and a human gene for type II procollagen (COL2A1). The 5'-end of the construct contains the promoter, exon 1 and intron 1 of the COL1A1 gene fused to intron 1 of the COL2A1 gene. The construct is designed so that the promoter and putative enhancer in the first intron of the COL1A1 drive expression of the COL2A1 gene and cause production of human type II procollagen. The COL2A1 gene consisted of two SphI/SphI fragments of the gene totalling about 26,000 base pairs. This construct contains all the coding sequences of the gene except for the few codons of a signal peptide in exon 1 and an alternatively spliced exon that follows exon 1. Some versions of the construct also include a 3,500 base pair SphI/SphI fragment from the 3'-end of the gene that is needed for correct polyadenylation of the mRNA.

A second construct has the promoter, the first exon, the intron, and about half of the second exon of the human COL1A1 gene as the 5'-fragment of the construct. The 5'-fragment is joined through a unique KpnI restriction endonuclease site to a cDNA that contains all the coding sequences of the gene except for those contained in the first one and one-half exons. In addition, the 3'-end of the cDNA is linked through an EcoRI site to an EcoRI/EcoRI fragment of about 0.5 kb from the 3'-end of the COL1A1 gene. A series of additional constructs use the highly active promoter for the cytomegalic virus to drive expression of full-length cDNA, for the human COL1A1 gene. All the constructs have been engineered so that they have unique restriction endonuclease sites at their 5'- and 3'-ends and, therefore, can be excised from vector sequences.

The present invention involves transfection and expression of collagen gene constructs in selected cells. Human tumor cells HT-1080 are preferred. However, the invention can also employ other cells that can be cultured and contain the necessary post translational enzymes and secretory mechanisms, such as chinese hamster ovary cells.

BRIEF DESCRIPTION OF THE DRAWINGS

FIG. 3 is a photograph showing analysis of medium of HT-1080 cells co-transfected with a gene for COL1A1 and a gene for COL1A2. THE COL1A2 was linked to an active neomycin-resistance gene but the COL1A1 was not. The cells were screened for expression of the COL1A2-neomycin resistance gene construct with the neomycin analog G418. The medium was analyzed for expression of the COL1A1 by Western blotting with a polyclonal antibody specific for the human proα1(I) chain. Lane 1 indicates that the medium proteins contained proα(I) chains. Lane 2 is an authentic standard of type I procollagen containing proα1(I) chains and partially processed pCα1(I) chains. The results demonstrate that the cells synthesized human type procollagen that contained proα1(I) chains, presumably in the form of the normal heterotrimer with the composition two proα(I) chains and one proα2(I) chain.

DETAILED DESCRIPTION OF THE INVENTION

Figure 1:
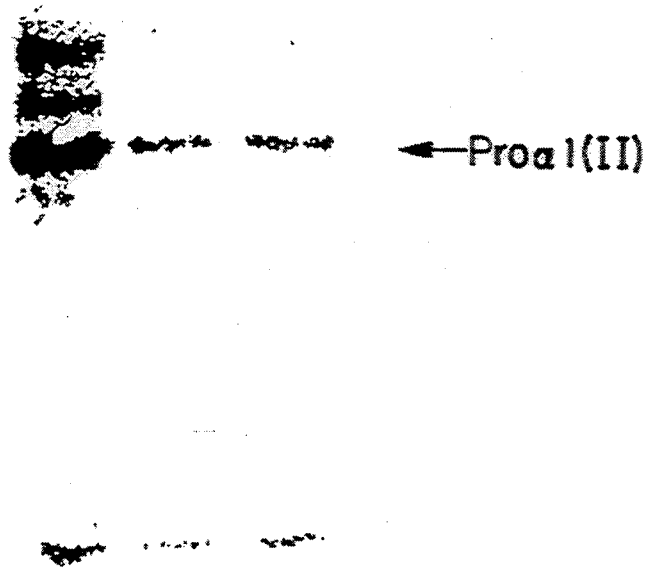
FIG. 1 is a photograph showing analysis by polyacrylamide gel electrophoresis in SDS of the proteins secreted into medium by HT-1080 cells that were stably transfected with a gene construct containing the promoter, first exon and most of the first intron of the human COL1A1 gene linked to 30 kb fragment containing all of COL2A1 except the first two exons. The cells were incubated with [$^{14}$C]proline so that the medium proteins could be analyzed by autoradiography (storage phosphor film analyzer). Lane 1 shows that the unpurified medium proteins are comprised of three major polypeptide chains. The upper two are proα1(IV) and proα2(IV) chains of type IV collagen that are synthesized by cells not transfected by the construct (not shown). The third band is the proα1(II) chains of human type II procollagen synthesized from the construct. Lanes 2 and 3 are the same medium protein after chromatography of the medium on an ion exchange column (DE-52, Whatman, at pH 7.4 in lane 2 and at pH 7.0 in lane 3). The type II procollagen appeared in the void volume of the ion exchange column.

It has been established that most forms of osteogenesis imperfecta (OI) are caused by dominant mutations in one of the two genes for type I procollagen. Also, at least a subset of post-menopausal osteoporosis is caused by similar mutations in the two genes for type II procollagen. It has further been reported that mutations in the type II procollagen gene cause human diseases such as chondrodysplasias, arthro-ophthalmopathy, known as Stickler's syndrome, and a subset of primary generalized osteoarthritis. It has further been reported that mutations in the type III procollagen gene (COL3A1) cause human diseases such as a lethal variant of Ehlers-Danlos syndrome (type IV) and familial aneurysms. Moreover, it has been demonstrated that the kidney disease known as the Alport syndrome is caused by mutations in one of the genes (COL4A5) for type IV collagen. It has further been demonstrated that injections of suspensions of collagen fibers are effective for the treatment of cosmetic defects as well as physical weakness of tissues such as sphinctors.

The present invention concerns cells in which one of these fibrillar procollagens is expressed both as mRNA and as a protein. Additionally, the present invention concerns types I, II, and III procollagens expressed in a human tumor cell line, and the establishment of stably transfected cell lines comprising these procollagen genes.

The present invention further provides that the gene constructs can be used to synthesize human fibrillar procollagens in the HT-1080 human tumor cell line (American Type Culture Collection, 12301 Parklawn Drive, Rockville, Md.; accession number CCL-121. This human cell line has been a ready source of type IV collagen, the major collagen of basement membranes. Because type IV collagen is not a fibril-forming procollagen or collagen, it can be readily separated by a simple chromatographic procedure from any fibrillar procollagen. Hence, the invention provides methods whereby a human fibrillar procollagen can be readily separated from products of an endogenous collagen gene. Moreover, HT-1080 cells grow extremely rapidly in culture and can be maintained for long periods of time.

Additionally, the present invention provides for a single procollagen or collagen gene or a number of different procollagen or collagen genes stably expressed within a cell. Further, it is contemplated that the there can be one or more copies of a single procollagen or collagen gene or of the number of different such genes transfected into cells and stably expressed. The present invention provides that these cells can be transfected with and stably express at least one human procollagen genes, especially but not limited to the COL1A1 gene encoding the proα1(I) procollagen chain of human type I procollagen. It is also provided that the cells can be transfected with and stably express both COL1A1 and COL1A2 genes so that both proα2(I) and proα1(I) chains are simultaneously synthesized and assembled into normal heterotrimeric molecules of type I procollagen. Moreover, the present invention provides that cells can be transfected with and stably express the COL2A1 gene encoding the proα1(II) chain of human type II procollagen. It is further provided that cells can be transfected with and stably express the COL3A1 gene encoding the proα1(III) chain of type III procollagen. The invention also provides that any procollagen or collagen gene transfected into and stably expressed within cells may comprise a mutant, variant, hybrid or recombinant gene. Further, the present invention provides transfected cells substantially all of which comprise other procollagen or collagen genes, preferably but not limited to types I, II, III procollogen genes or type IV collagen genes. The present invention contemplates that transfected cells may be human tumor cells, especially but not limited to HT-1080 cells. The present invention further contemplates cells substantially all of which comprise at least one transfected human procollagen or collagen gene having at least one chain derived from a transfected or collagen procollagen gene or genes and at least one chain derived from an endogenous human or non-human procollagen gene or genes, other than the [proα1(I)]₂proα2(I) collagen molecule consisting of human proα1(I) moieties and non-human proα2(I) moieties, or non-human proα1(I) moieties and human proα2(I) moieties.

A novel feature of the methods of the invention is that relatively large amounts of a human fibrillar procollagen can be synthesized in a recombinant cell culture system that does not make any other fibrillar procollagen. Systems that make other fibrillar procollagens or collagens are impractical because of the extreme difficulty of purifying the product of the endogenous genes for fibrillar procollagen or collagen from products of the recombinant genes. Using methods of the present invention purification of human procollagen is greatly facilitated. Moreover, it has been demonstrated that the amounts of protein synthesized by the methods of the present invention are high relative to other systems used in the art.

Other novel features of the methods of present invention are that procollagens synthesized are correctly folded proteins so that they exhibit the normal triple-helical conformation characteristic of procollagens and collagens. Therefore the procollagens can be used to generate stable collagen fibrils and fibers by cleavage of the procollagens with proteases.

The present invention is in contrast to Schnieke et al., who reported that a gene for the human fibrillar procollagen proα1(I) chain, the COL1A1 gene, can be expressed in mouse fibroblasts and the chains used to assemble molecules of type I procollogen, the precursor of type I collagen. However, in the system of Schnieke et al., the proα2(I) chains found in the molecule of type I procollagen were of mouse origin. Hence, the type I procollagen synthesized is a hybrid molecule of human and mouse origin. Similarly, the system of Lee et al. expressed an exogenous proα2(I) gene to generate type I procollagen in which the proα1(I) chains were of rat origin. The present invention provides methods for the production of procollagens or collagens derived solely from transfected procollagen and collagen genes, but these methods are not limited to the production of procollogen and collagen derived solely from transfected genes.

An advantage of human collagens of the present invention is that these collagens will not produce allergic responses in man. Moreover, collagen of the present invention prepared from cultured cells should be of a higher quality than collagen obtained from animal sources, and should form larger and more tightly packed fibers. These higher quality proteins should form deposits in tissues that last much longer than the currently available commercial materials. It is known that using currently available methods, most injections of collagen for cosmetic purposes have to be repeated as frequently as every 6 months. Human protein of the present invention should last much longer after injection into human tissues.

Methods of the present invention provide a practical source of a human fibrillar collagen similar to animal collagens that are widely used for injection to remove cosmetic wrinkles, and cosmetic defects of other natures, and are also being used to restore the tensile strength of tissues such as the sphincter of the bladder in the treatment of urinary incontinence. Type I collagen from animal sources has been used commercially. However, a convenient source of human collagen for therapeutic use is still sorely needed.

Further, the present invention contemplates that human type II procollagen, the precursor of the major collagen of cartilage may have special use in the repair of cartilage damage. Moreover, modified human type I procollagen comprising a proα1(I) trimer expressed according to the methods in the present invention is also contemplated. Also, type I procollagen comprised of two proα1(I) and one proα2(I) chains derived from transfected human genes is contemplated. Also, type III procollagen comprised of three proα1(III) chains derived from transfected human genes is contemplated.

Methods are provided for synthesizing fibrillar collagen in cells comprising transfecting at least one human procollagen or collagen gene into cells and selecting transfected cells that comprise molecules derived from a procollagen or collagen gene or genes, other than the [proα1(I)]$_2$proα2(I) molecule consisting of human proα1(I) moieties and non-human proα2(I) moieties, or non-human α1(I) moieties and human α2(I) moieties. Further, methods whereby at least one of the human procollagen genes is a mutant, variant, hybrid or recombinant gene are also contemplated. Additionally, the present invention provides methods whereby substantially all cells transfected with at least one procollagen gene comprise type III and other procollagen genes. Further, methods are contemplated wherein transfected cells are human tumor cells, especially but not limited to HT-1080 cells. Methods are also provided whereby transfected cells comprise independently substantially no endogenously derived collagen molecules, endogenously derived type I procollagen molecules, endogenously derived type II procollagen molecules, endogenously derived type III procollagen molecules, or endogenously derived type IV collagen molecules. Other methods are provided whereby substantially all of the transfected cells comprise at least one transfected human procollagen gene and express procollagen or collagen molecules having at least one chain derived from the transfected gene, other than the [proα1(I)]$_2$proα2(I) collagen consisting of human proα1(I) moieties and non-human proα2(I) moieties, or non-human proα1(I) moieties and human proα2(I) moieties. Other preferred methods are provided whereby substantially all transfected cells comprise at least one transfected human procollagen gene and express procollagen molecules having three chains derived from the transfected collagen gene or genes.

The present invention is further illustrated by the following examples, which are not intended to be limiting in any way.

EXAMPLES

Example 1 Synthesis of Human Type II Procollagen

A recombinant COL1A1 gene construct employed in the present invention comprised a fragment of the 5'-end of COL1A1 having a promotor, exon 1 and intron 1 fused to exons 3 through 54 of a COL2A1 gene. The hybrid construct was transfected into HT-1080 cells. These cells were co-transfected with a neomycin-resistance gene and grown in the presence of the neomycin analog G418. The hybrid construct was used to generate stably transfected cells.

Figure 2:
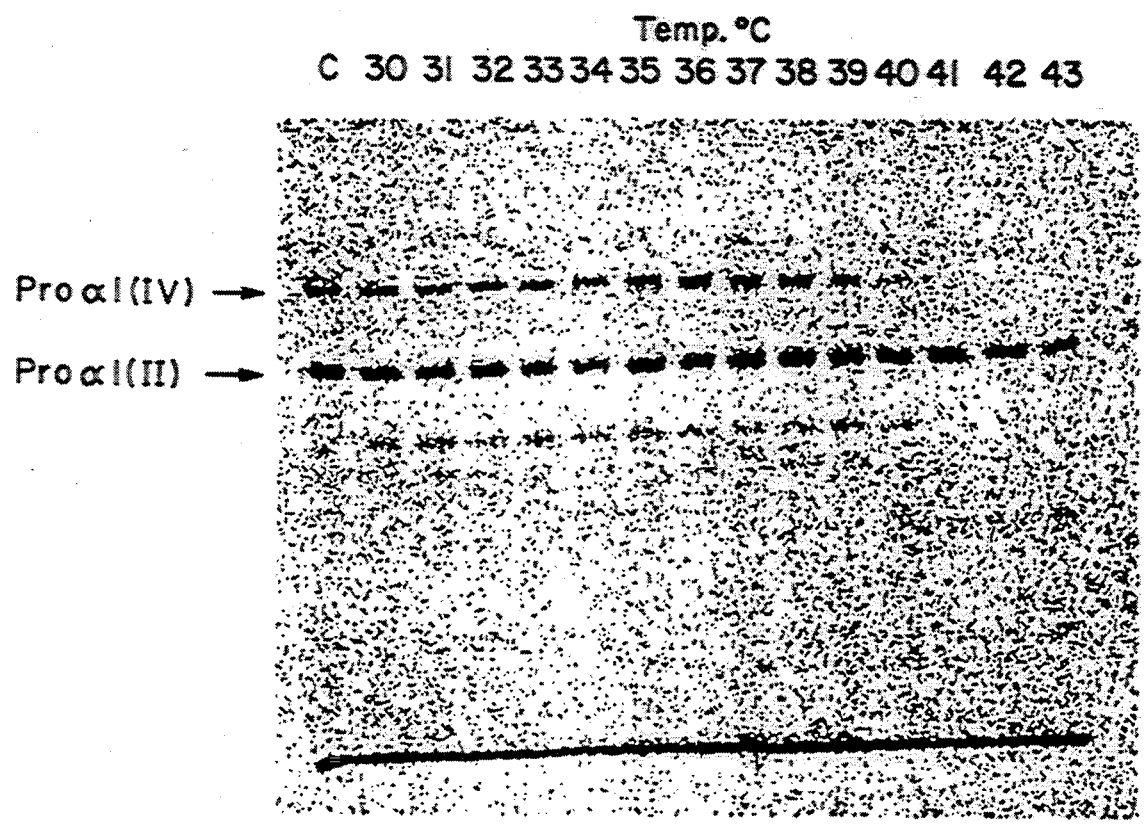
FIG. 2 is a photograph showing that the type II procollagen secreted into the medium from cells described in FIG. 1 was folded into a correct native conformation. The medium proteins were digested at the temperatures indicated with a high concentration of trypsin and chymotrypsin under conditions in which correctly folded triple-helical procollagen or collagen resists digestion but unfolded or incorrectly folded procollagen of collagen is digested to small fragments (Bruckner and Prockop, Anal. Biochemistry 110:360 (1981)). The products of the digestion were then analyzed by polyacrylamide gel electrophoresis in SDS and fluorography. The results show that the type II procollagen resisted digestion up to 43° C., the normal temperature at which type II procollagen unfolds. Therefore, the type II procollagen is correctly folded and can be used to generate collagen fibrils.

A series of clones were obtained that synthesized mRNA for human type II procollagen. To analyze the synthesized proteins, the cells were incubated with [$^{14}$C]proline and the $^{14}$C-labeled medium proteins were analyzed by gel electrophoresis. See FIG. 1. As indicated in Lane 1, the medium proteins contained the expected type II procollagen comprised of proα1(II) chains together with proα1(IV) and proα2(IV) chains of type IV collagen normally synthesized by the cells. As indicated in Lanes 2 and 3, the type II procollagen was readily purified by a single step of ion exchange chromatography. The type II procollagen secreted into the medium was correctly folded by a protease-thermal stability test. See FIG. 2.

Example 2 Synthesis of Human Type I Procollagen

Figure 3:
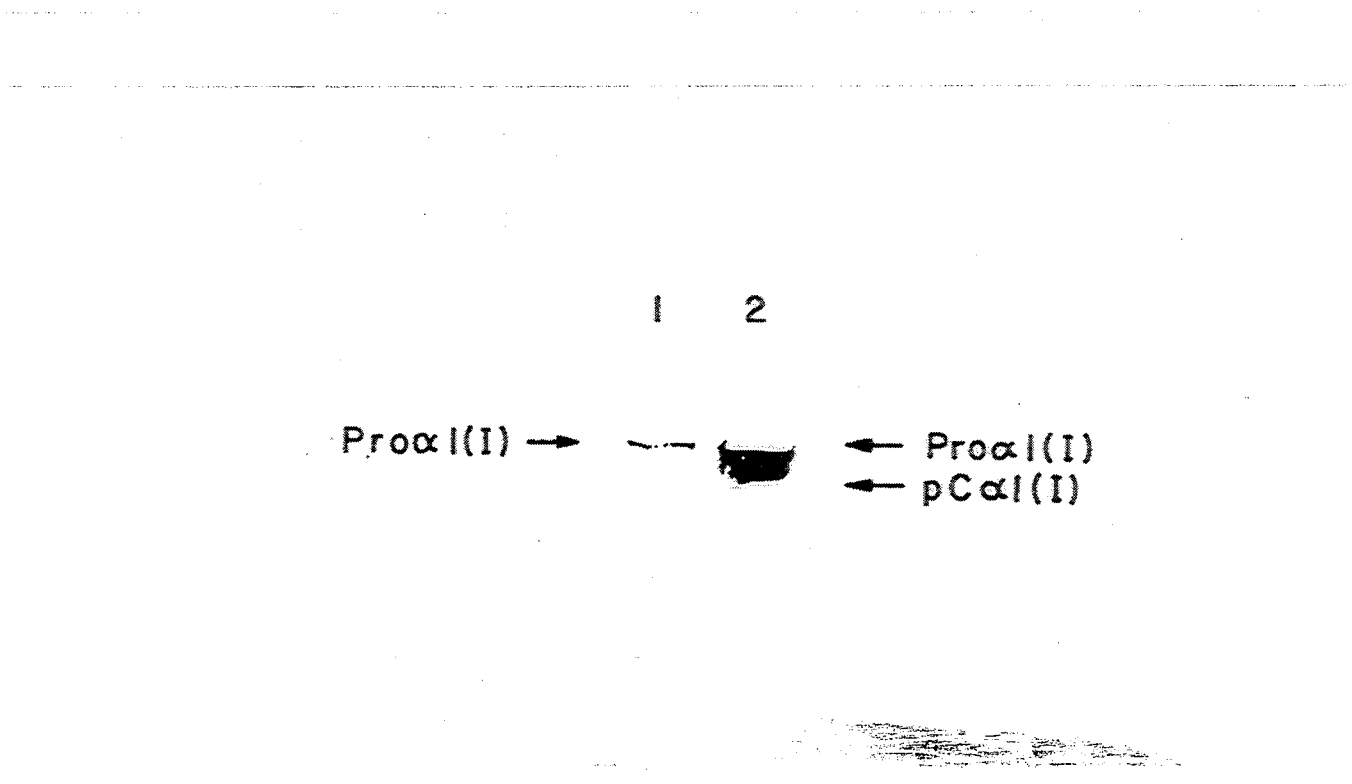

As a second example, HT-1080 cells were co-transfected with a COL1A1 gene and a COL1A2 gene. Both genes consisted of a cytomegalic virus promoter linked to a full-length cDNA. The COL1A2 gene construct but not the COL1A1 gene construct contained a neomycin-resistance gene. The cells were selected for expression of the COL1A2-neomycin resistance gene construct by growth in the presence of the neomycin-analog G418. The medium was then examined for expression of the COL1A1 with a specific polyclonal antibody for human proα1(I) chains. The results (see FIG. 3.) demonstrated that the cells synthesized human type I procollagen that was probably comprised of the normal heterotrimeric structure of two proα1(I) chains and one proα2(I) chain.

Table 1 presents a summary of the DNA constructs containing human procollagen genes. The constructs were assembled from discrete fragments of the genes or cDNAs from the genes together with appropriate promoter fragments.

II collagen. See Cheah et al., Proc. Natl. Acad. Sci. USA, 82:2555–2559 (1985). The antibody did not react by Western blot analysis with proα chains of human type I procollagen or collagen, human type II procollagen or collagen, or murine type I procollagen. For assay of expression of the COL1A1 genes, polyclonal antibodies that reacted with the COOH-terminal polypeptide of the proα1(I) chain were employed. See Olsen et al., J. Biol. Chem., 266:1117–1121 (1991).

Culture medium from pooled clones or individual clones was removed and separately precipitated by the addition of solid ammonium sulfate to 30% saturation and precipitates were collected by centrifugation at 14,000×g and then dialyzed against a buffer containing 0.15M NaCl, 0.5mM EDTA, 0.5 mM N-ethylmalei-

TABLE 1

| Constructs | 5'-end | Central Region | 3'-end | Protein product |
|---|---|---|---|---|
| A | Promoter (2.5 kb) + exon 1 + intron 1 from COL1A1 | Exons 3 to 54 from COL2A1 | 3.5 kb SphI/SphI fragment from 3'-end of COL2A1 | Human type II procollagen, [proα1(II)]₃ |
| B | Promoter (2.5 kb) of COL1A1 | Exons 1 to 54 from COL2A1 | 3.5 kb SphI/SphI fragment from 3'-end of COL2A1 | Human type II procollagen, [proα1(II)]₃ |
| C | Promoter (2.5 kb) + exon 1 + intron 1 + half of exon 2 from COL1A1 | cDNA for COL1A1 except for first 1 1/2 exons | 0.5 kb fragment from COL1A1 | Human type I procollagen, [proα1(I)]₃ |
| D | Cytomegalic virus promoter | cDNA from COL1A1 | | Human type I procollagen, [proα1(I)]₃ |
| E | Cytomegalic virus promoter | cDNA from COL1A2 | | Human type I [proα1(I)]₂proα2(I)] when expressed with construct C or D |

Example 3 Cell Transfections

For cell transfection experiments, a cosmid plasmid clone containing the gene construct was cleaved with a restriction endonuclease to release the construct from the vector. A plasmid vector comprising a neomycin resistance gene, Law et al., Molec. Cell Biol., 3:2110–2115 (1983), was linearized by cleavage with BamHI. The two samples were mixed in a ratio of approximately 10:1 gene construct to neomycin-resistant gene, and the mixture was then used for co-transfection of HT-1080 cells by calcium phosphate co-precipitation, Sambrook et al., Molecular Cloning. A Laboratory Manual, Cold Spring Harbor Laboratory Press, Second Edition (1989). DNA in the calcium phosphate solution was layered onto cultured cells with about 10 μg of chimeric gene construct per 100 ml plate of preconfluent cells. Cells were incubated in DMEM containing 10% newborn calf serum for 10 hours. The samples were subjected to glycerol shock by adding a 15% glycerol solution for 3 minutes. The cells were then transferred to DMEM medium containing newborn calf serum for 24 hours and then to the same medium containing 450 ug/ml of G418. Incubation in the medium containing G418 was continued for about 4 weeks with a change of medium every third day. G418-resistant cells were either pooled or separate clones obtained by isolating foci with a plastic cylinder and subcultured.

Example 4 Western Blotting

For assay of expression of the COL2A1 gene, polyclonal antibodies were prepared in rabbits using a 23-residue synthetic peptide that had an amino acid sequence found in the COOH-terminal telopeptide of type mide, 0.1 mM and p-aminobenzamidine, and 50 mM Tris-HCl (pH 7.4 at 4° C.). Aliquots of the samples were heated to 10° C. for 5 minutes in 1% SDS, 50 mM DTT and 10% (v/v) glycerol, and separated by electrophoresis on 6% polyacrylamide gels using a mini-gel apparatus (Holford SE250, Holford Scientific) run at 125 V for 90 minutes. Separated proteins were electroblotted from the polyacrylamide gel at 40 V for 90 minutes onto a supported nitrocellulose membrane (Schleicher and Schuell). The transferred proteins were reacted for 30 minutes with the polyclonal antibodies at a 1:500 (v/v) dilution. Proteins reacting with the antibodies were detected with a secondary anti-rabbit IgG antibody coupled to alkaline phosphatase (Promega Biotech) for 30 minutes. Alkaline phosphatase was visualized with NBT/BCIP (Promega Biotech) as directed by the manufacturer.

Example 5 Demonstration of Correct Folding of the Secreted Procollagens

To demonstrate that the procollagens synthesized and secreted in the medium by the transfected cells were correctly folded, the medium proteins were digested with high concentrations of proteases under conditions in which only correctly folded procollagens and collagens resist digestion. For digestion with a combination of trypsin and chymotrypsin, the cell layer from a 25 cm flask was scraped into 0.5 ml of modified Krebs II medium containing 10 mM EDTA and 0.1% Nonidet P-40 (Sigma). The cells were vigorously agitated in a Vortex mixer for 1 minute and immediately cooled to 4° C. The supernatant was transferred to new tubes. The sample was preincubated at the temperature indicated for 10 minutes and the digestion was carried out at the same temperature for 2 minutes. For the digestion, a 0.1 volume of the modified Krebs II medium containing 1 mg/ml trypsin and 2.5 mg/ml α-chymotrypsin (Boehringer Mannheim) was added. The digestion was stopped by adding a 0.1 volume of 5 mg/ml soybean trypsin inhibitor (Sigma).

For analysis of the digestion products, the sample was rapidly immersed in boiling water for 2 minutes with the concomitant addition of a 0.2 volume of 5×electrophoresis sample buffer that consisted of 10% SDS, 50% glycerol, and 0.012% bromphenol blue in 0.625M Tris-HCl buffer (pH 6.8). Samples were applied to SDS gels with prior reduction by incubating for 3 minutes in boiling water after the addition of 2% 2-mercaptoethanol. Electrophoresis was performed using the discontinuous system of Laemmli (Nature, 227:680–685 (1970) with minor modifications described by de Wet et al., (Journal of Biological Chemistry, 258:7721–7728 (1983))

What is claimed:

1. Human tumor cells substantially all of which comprise at least one transfected human proα1(I) procollagen gene or human proα1(I) collagen gene, and which express human procollagen or human collagen molecules having at least one chain derived from said transfected human procollagen or human collagen gene or genes, wherein any chains derived from genes other than said transfected human genes are derived from expression of endogenous genes.

2. The human tumor cells of claim 1 having three chains derived from said transfected gene or genes.

3. A method for synthesizing procollagen or collagen in human tumor cells comprising the steps of:
   a) transfecting at least one human proα1(I) procollagen gene or human proα1(I) collagen gene into said human tumor cells,
   b) culturing said human tumor cells under conditions such that said transfected human procollagen gene or transfected human collagen gene are expressed;
   c) selecting transfected humor tumor cells that comprise at least one transfected human proα1(I) procollagen gene or human proα1(I) collagen gene, and which express human procollagen or human collagen molecules having at least one chain derived from said transfected human procollagen or human collagen gene or genes, wherein any chains derived from genes other than said transfected human genes are derived from expression of endogenous genes.

4. Human tumor cells substantially all of which comprise at least one transfected gene that encodes human proα1(I) procollagen or human proα1(I) collagen and at least one transfected gene that encodes human proα2(I) procollagen or human proα2(I) collagen, wherein said human tumor cells express human type I procollagen [proα1(I)$_2$]proα2(I) molecules.

5. The human tumor cells of claim 1 wherein said human tumor cells are HT-1080 cells.

6. The human tumor cells of claim 1 wherein said human tumor cells are transfected with a full length cDNA encoding a human pro1(I) procollagen.

7. The human tumor cells of claim 6 wherein said human tumor cells are HT-1080 cells.

8. The human tumor cells of claim 6 wherein said human tumor cells are transfected with a full length cDNA encoding human proα1(I) procollagen operably linked to a cytomegalovirus promoter.

9. The human tumor cells of claim 8 wherein said human tumor cells are HT-1080 cells.

10. The human tumor cells of claim 6 wherein said human tumor cells are transfected with a full length cDNA encoding human proα2(I) procollagen operably linked to a cytomegalovirus promoter.

11. The human tumor cells of claim 10 wherein said human tumor cells are HT-1080 cells.

12. The human tumor cells of claim 2 wherein said human tumor cells are HT-1080 cells.

13. The human tumor cells of claim 2 wherein said human tumor cells are transfected with a full length cDNA encoding a human pro1(I) procollagen.

14. The human tumor cells of claim 13 wherein said human tumor cells are HT-1080 cells.

15. The human tumor cells of claim 2 wherein said human tumor cells are transfected with a full length cDNA encoding human proα1(I) procollagen operably linked to a cytomegalovirus promoter.

16. The human tumor cells of claim 15 wherein said human tumor cells are HT-1080 cells.

17. The human tumor cells of claim 2 wherein said human tumor cells are transfected with
   a) a full length cDNA encoding human proα1(I) procollagen operably linked to a cytomegalovirus promoter, and
   b) a full length cDNA encoding human proα2(I) procollagen operably linked to a cytomegalovirus promoter.

18. The human tumor cells of claim 17 wherein said human tumor cells are HT-1080 cells.

19. The method of claim 3 wherein said human tumor cells are HT-1080 cells.

20. The method of claim 3 wherein said human tumor cells are transfected with a full length cDNA encoding a human pro1(I) procollagen.

21. The method of claim 20 wherein said human tumor cells are HT-1080 cells.

22. The method of claim 20 wherein said human tumor cells are transfected with a full length cDNA encoding human proα1(I) procollagen operably linked to a cytomegalovirus promoter.

23. The method of claim 22 wherein said human tumor cells are HT-1080 cells.

24. The method of claim 22 wherein said human tumor cells are transfected with a full length cDNA encoding human proα2(I) procollagen operably linked to a cytomegalovirus promoter.

25. The method of claim 24 wherein said human tumor cells are HT-1080 cells.

* * * * *